(12) United States Patent
Ingram et al.

(10) Patent No.: US 9,028,438 B2
(45) Date of Patent: May 12, 2015

(54) ENTERAL FEEDING AND REFLUX COLLECTION SYSTEM AND METHOD USING VENTED SYRINGE

(71) Applicant: NeoMed, Inc., Woodstock, GA (US)

(72) Inventors: Aaron N. Ingram, Canton, GA (US); Anthony C. Lair, Alpharetta, GA (US)

(73) Assignee: NeoMed, Inc., Woodstock, GA (US)

( * ) Notice: Subject to any disclaimer, the term of this patent is extended or adjusted under 35 U.S.C. 154(b) by 238 days.

(21) Appl. No.: 13/655,780

(22) Filed: Oct. 19, 2012

(65) Prior Publication Data

US 2013/0066260 A1    Mar. 14, 2013

Related U.S. Application Data

(63) Continuation-in-part of application No. 13/231,185, filed on Sep. 13, 2011.

(60) Provisional application No. 61/549,308, filed on Oct. 20, 2011, provisional application No. 61/418,963, filed on Dec. 2, 2010.

(51) Int. Cl.
| | |
|---|---|
| *A61M 1/00* | (2006.01) |
| *A61M 31/00* | (2006.01) |
| *A61M 5/145* | (2006.01) |
| *A61J 15/00* | (2006.01) |

(Continued)

(52) U.S. Cl.
CPC ............ *A61M 31/00* (2013.01); *A61M 5/1452* (2013.01); *A61M 5/1456* (2013.01); *A61J 15/0096* (2013.01); *A61M 5/3135* (2013.01); *A61M 2005/3123* (2013.01); *A61M 2039/0255* (2013.01); *A61M 2210/1021* (2013.01); *A61J 15/00* (2013.01); *A61J 2200/76* (2013.01)

(58) Field of Classification Search
CPC ................ A61J 15/00; A61J 15/0096; A61M 2005/3123; A61M 2039/0255
USPC ........................................ 604/910, 35, 27, 19
See application file for complete search history.

(56) References Cited

U.S. PATENT DOCUMENTS

| | | | |
|---|---|---|---|
| 4,356,824 | A | 11/1982 | Vazquez |
| 4,392,851 | A | 7/1983 | Elias |
| 5,460,603 | A | 10/1995 | DeSantis |

(Continued)

FOREIGN PATENT DOCUMENTS

| | | |
|---|---|---|
| DE | 29617949 U1 | 4/1997 |
| EP | 0481250 A1 | 4/1992 |

(Continued)

OTHER PUBLICATIONS

International Search Report and Written Opinion for PCT/US2012/060987; Jan. 25, 2013; 13 pgs.

(Continued)

*Primary Examiner* — Nicholas Lucchesi
*Assistant Examiner* — Deanna K Hall
(74) *Attorney, Agent, or Firm* — Gardner Groff Greenwald & Villanueva, PC

(57) ABSTRACT

An enteral fluid delivery and reflux collection system and method are disclosed. A fluid nutrient source container and administration tube are joined to an enteral feeding tube, and a gastric reflux tube connects a vented reflux collection syringe to selectively permit or prevent reflux collection, and/or to aspirate or flush the associated fluid lines.

15 Claims, 4 Drawing Sheets

(51) Int. Cl.
  *A61M 5/31*     (2006.01)
  *A61M 39/02*    (2006.01)

(56) References Cited

U.S. PATENT DOCUMENTS

| | | | |
|---|---|---|---|
| 5,611,787 A | 3/1997 | Demeter et al. | |
| 6,482,170 B1* | 11/2002 | Andersen | 604/27 |
| 7,174,923 B2* | 2/2007 | Schorn et al. | 141/2 |
| 7,842,217 B2 | 11/2010 | Enns et al. | |
| 8,162,916 B2 | 4/2012 | Knight | |
| 8,231,597 B2 | 7/2012 | Knight | |
| 2004/0054350 A1 | 3/2004 | Shaughnessy et al. | |
| 2008/0097348 A1 | 4/2008 | Itrich | |
| 2010/0204669 A1 | 8/2010 | Knight | |
| 2011/0046568 A1 | 2/2011 | Enns et al. | |
| 2011/0270227 A1 | 11/2011 | Kleckner et al. | |
| 2012/0071853 A1 | 3/2012 | Ingram et al. | |
| 2012/0150111 A1 | 6/2012 | Hershey et al. | |
| 2012/0150112 A1 | 6/2012 | Hershey et al. | |
| 2012/0289936 A1 | 11/2012 | Ingram et al. | |

FOREIGN PATENT DOCUMENTS

| | | |
|---|---|---|
| WO | 2007095541 A2 | 8/2007 |
| WO | 2009141510 A1 | 11/2009 |
| WO | 2012037082 A1 | 3/2012 |

OTHER PUBLICATIONS

International Search Report and Written Opinion for PCT/US2011/045481; Jan. 4, 2012; 19 pgs.

* cited by examiner

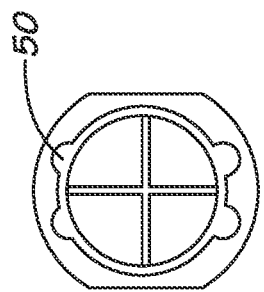
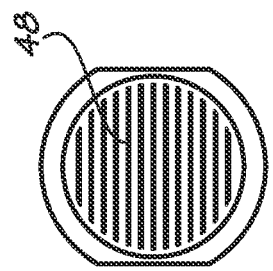
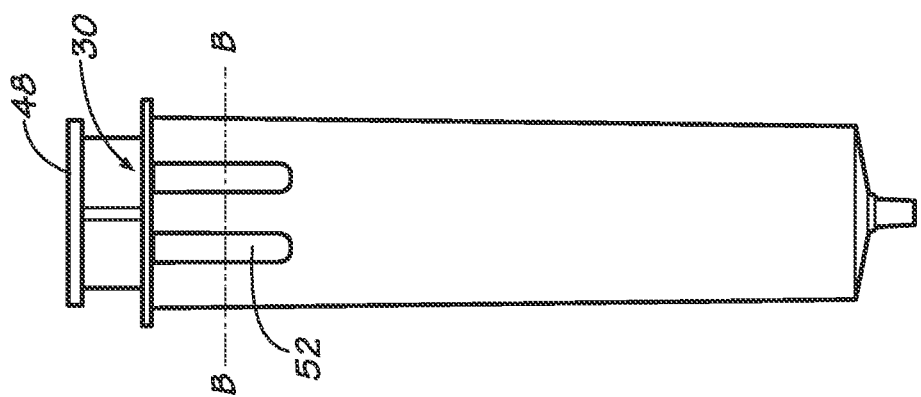
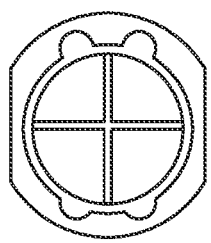
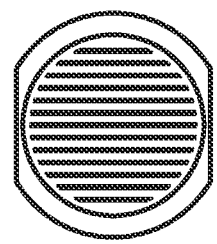
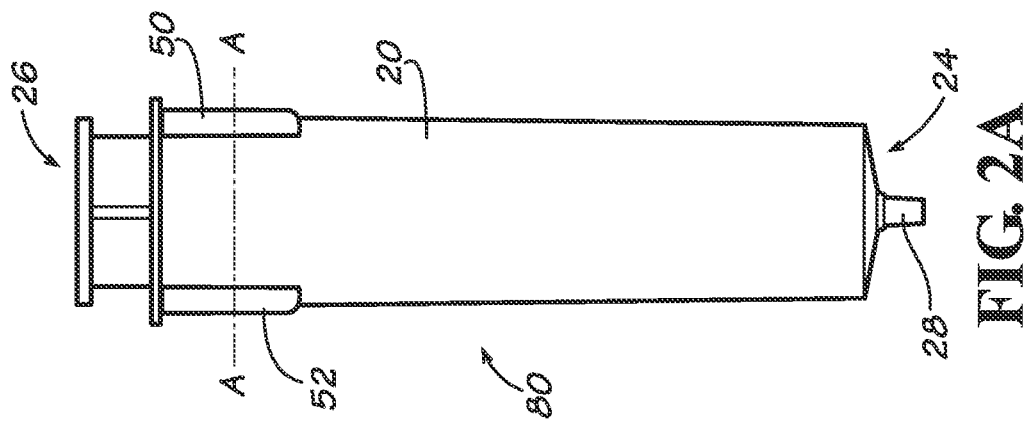

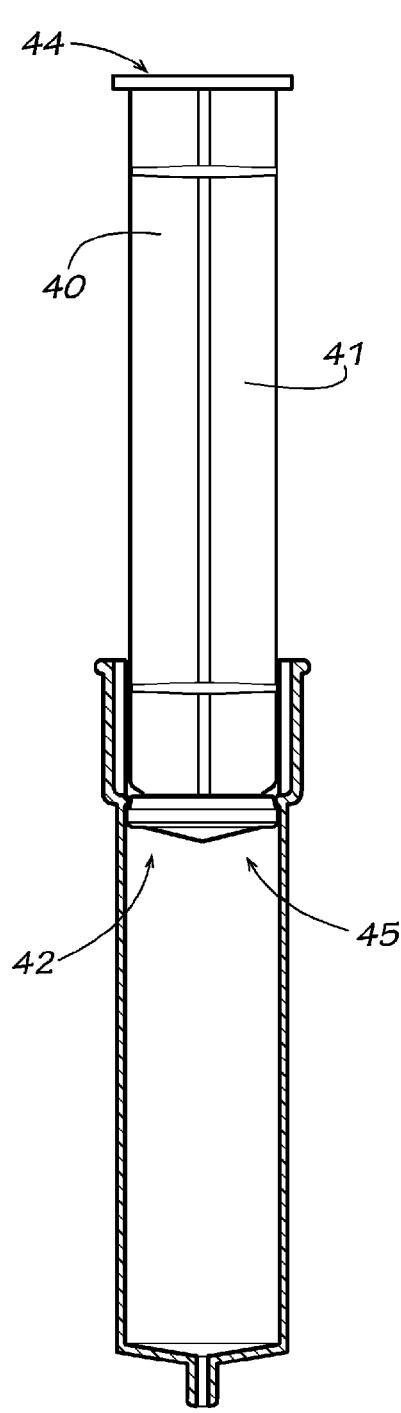
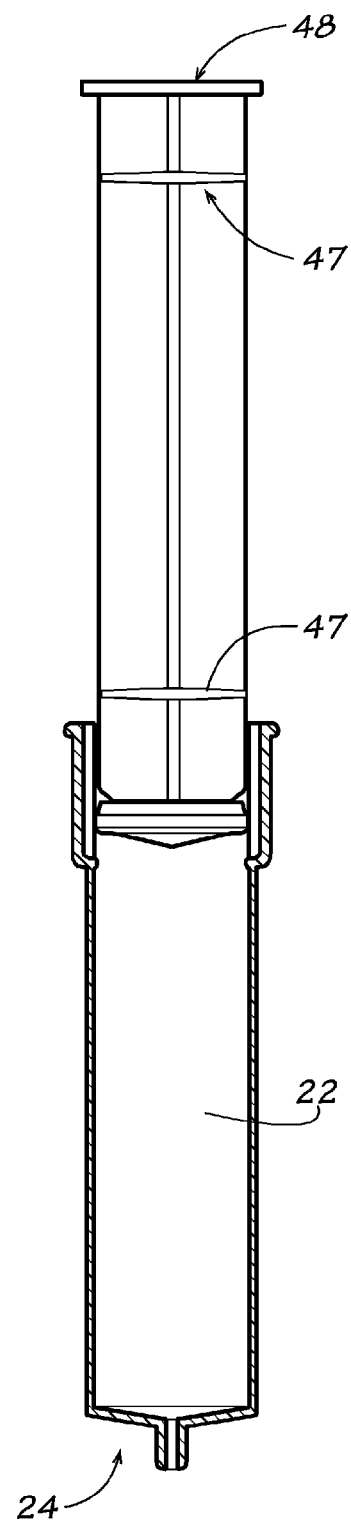
FIG. 3A  FIG. 3B

ENTERAL FEEDING AND REFLUX COLLECTION SYSTEM AND METHOD USING VENTED SYRINGE

CROSS-REFERENCE TO RELATED APPLICATION

This application claims the priority benefit of U.S. Provisional Patent Application Ser. No. 61/549,308 filed Oct. 20, 2011, which is hereby incorporated by reference herein; and this application is a continuation-in-part of U.S. patent application Ser. No. 13/231,185 filed Sep. 13, 2011, which claims priority to U.S. Provisional Patent Application Ser. No. 61/418,963 filed Dec. 2, 2010, the entireties of which are also hereby incorporated by reference herein.

TECHNICAL FIELD

The present invention relates generally to the field of enteral nutrition, and more particularly to an improved system and method for relieving gastric pressure in a human or animal patient during enteral feeding.

BACKGROUND

Enteral feeding systems are generally utilized to supply nutrition to the human gastrointestinal tract through an enteral feeding tube. For example, in the field of enteral feeding systems, optional delivery methods can include an enteral pump, syringe pump, or gravity feed delivery system. Optionally, a gastric pressure relief system can be used in conjunction with enteral feeding systems, for example when the subject is susceptible to reflux.

The gastric pressure relief system generally comprises a gastric reflux container, usually a vented disposable bag suspended above the stomach of the user, providing a reservoir for reflux gas and fluids to collect. The relief system can include an inlet/outlet port comprising a length of relief tubing that connects to the enteral feeding system. When administering nutrients to a user, the gastric reflux stomach contents intended to collect in the relief system can obtain trapped air pockets or gas bubbles clogging the relief tube. The stomach contents prevent further reflux to flow in the relief system and require disconnecting and cleaning the relief tube. The removal of the relief system from the enteral feeding system is often seen as a drawback to enteral administration and can severely alter the users feeding regimen. Additionally, undergoing an alteration mid-feeding can potentially waste much needed nutrients.

It is to the provision of an improved system and method for enteral gastric pressure relief and collection meeting these and other needs that the present invention is primarily directed.

SUMMARY

In example embodiments, the present invention selectively provides ventilation, vacuum and suction within the reflux collection system during use. The reflux collection system of the present invention can be utilized with the administration of various types of fluids to patients, such as medications, nutrients, food, water, etc. In particular, it has been found that the reflux collection system of the present invention greatly improves the administration of nutrients and/or medications when used in conjunction with pump, syringe pump, or gravity-fed enteral feeding systems.

In one aspect, the present invention relates to an enteral reflux collection system having a fluid container with a discharge. The system also has an enteral feeding tube for delivering fluid from the fluid container and a vented reflux collection syringe. The system also has a reflux relief tube for delivering reflux to the vented reflux syringe. The reflux relief tube is coupled with respect to the enteral feeding tube.

In another aspect, the present invention relates to an enteral reflux collection system for use with an enteral fluid container having a discharge and a feeding tube. The enteral reflux collection system includes a gastric reflux collection syringe with a confined internal cavity and a plunger. The system also includes a reflux relief tube to deliver gastric reflux to the gastric reflux collection syringe. The reflux relief tube is coupled with respect to the feeding tube.

In another aspect, the invention relates to a method for enteral fluid delivery, the method including the steps of delivering a fluid from a container to an enteral feeding tube, and selectively positioning a vented reflux collection syringe to alternatively permit or prevent gastric reflux collection within the syringe, or to aspirate fluid through one or more associated fluid delivery tubes.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIGS. 2A-2F show a vented syringe suited for use in connection with the system and method of the present invention according to an example form.

FIGS. 3A and 3B show cross-sectional views of the vented syringe of FIG. 2.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
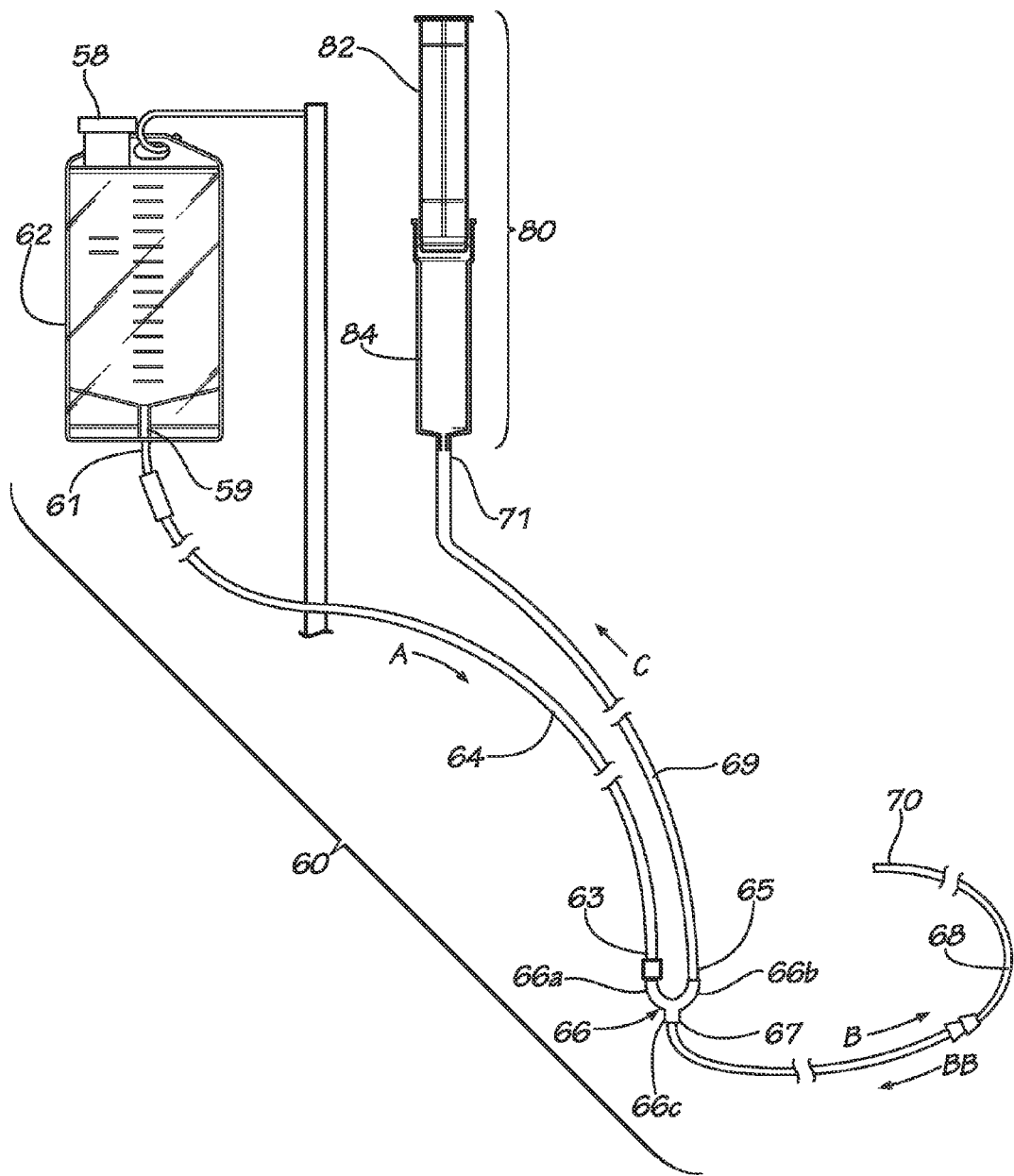
FIG. 1 shows an enteral reflux collection system according to a first example embodiment of the present invention incorporated with an enteral feeding system.

With reference now to the drawing figures, FIG. 1 shows an enteral feeding system 60 including a vented enteral reflux collection syringe 80 according to an example form of the invention. In general, the enteral feeding system 60 comprises an enteral feeding container or bag 62, a plurality of tubes 64, 68, and 69, and a Y-connector or coupling 66. The feeding bag 62, intended for containing the nutrients/medications to be supplied to the patient, optionally includes a removably accessible opening 58 and an outlet port 59. The outlet port 59 is sized to receive a proximal end 61 of an administration tube 64. A distal end 63 of the administration tube inserts into a first arm 66a of the connector 66. A proximal end 65 of a gastric relief tube 69 inserts into an arm segment 66b of the connector 66, and a proximal end 67 of an enteral feeding tube 68 inserts into an arm segment 66c of the connector. A distal end 71 of the gastric relief tube 69 connects to the enteral reflux collection syringe 80, which is preferably supported at a higher elevation than the connector 66 and higher than the discharge of the feeding bag 62, for example the discharge port 59. The enteral feeding tube 68, connected to the arm segment 16c of connector 66, further comprises a distal end 70 to provide interaction with a user and is preferably at an elevation above connector 66 and below the collection system 80.

The standard flow direction of nutrients through the feeding system is indicated by arrows A, B, BB, and C. The nutrients contained in the feeding bag 62 flow in the A direction through the administration tube 64. The nutrients enter the connector 66 through connector arm 66a and continue towards the proximal end 70 of enteral feeding tube 68 indicated by a direction arrow B, and are delivered to the digestive tract of the subject. In the event of gastric reflux from the subject, the nutrients may flow back through the proximal end 70 in the opposing direction BB, and through reflux tube 69 for collection in the reflux collection syringe 80, as indicated by direction arrow C. In alternate embodiments, the enteral feeding system of the present invention can comprise an enteral syringe used in place of the feeding bag. The enteral syringe can be vented to allow gravity feed by removing the plunger from the syringe body or placement of the plunger in the vent position within the syringe barrel.

Figure 4A:
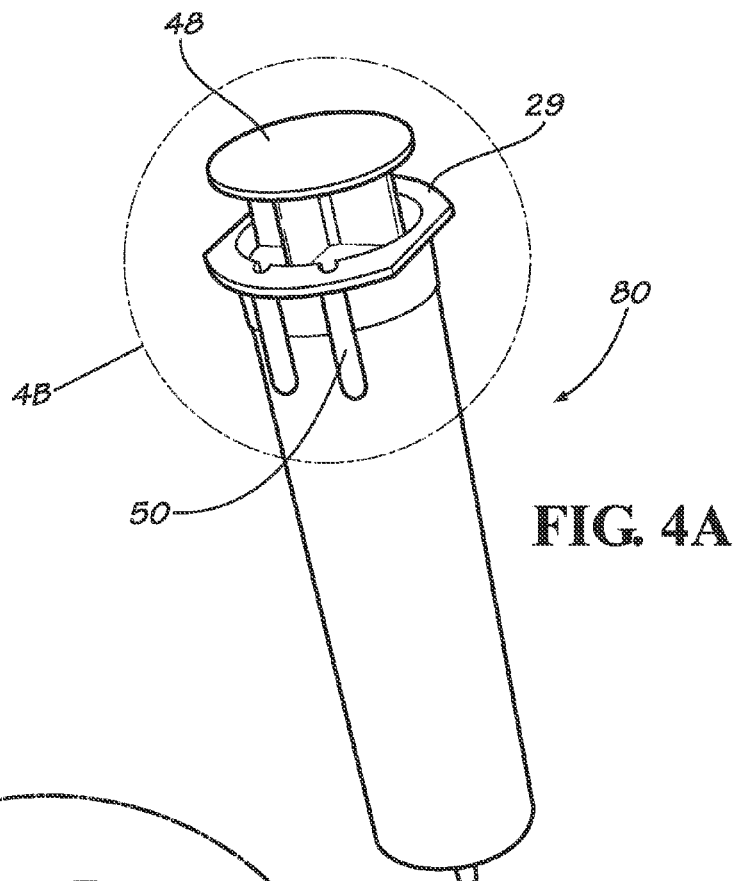
FIGS. 4A and 4B show perspective views of the vented syringe of FIG. 2.
Figure 4B:
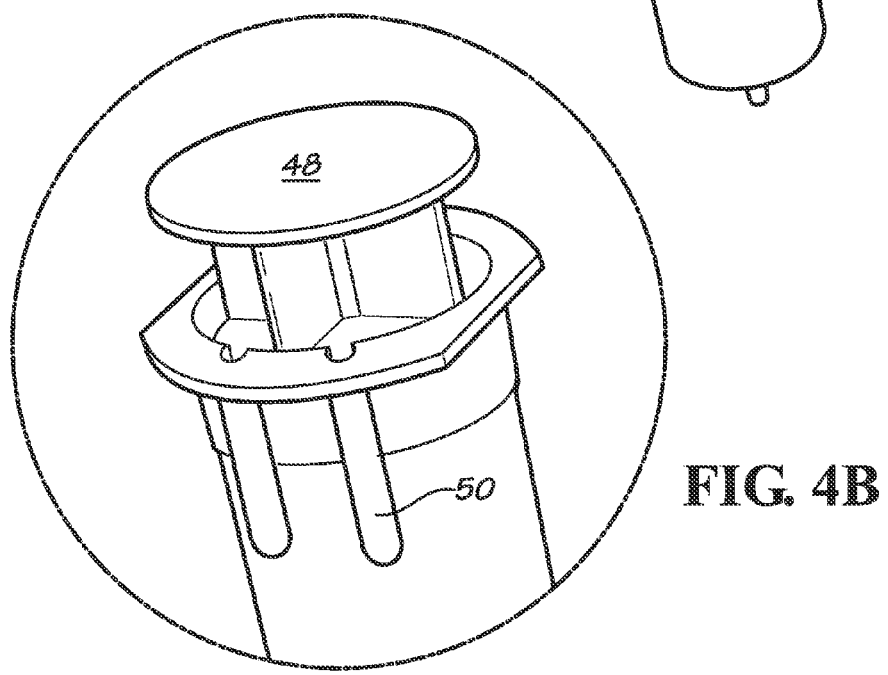

FIGS. 2-4 show a vented reflux collection syringe 80, according to an example form, in greater detail. U.S. patent application Ser. No. 13/231,185 and U.S. Provisional Patent Application Ser. No. 61/418,963 are incorporated herein for further details of an example form of syringe construction. The vented reflux collection syringe 80 includes an elongated syringe body 20 and a plunger 40. The syringe body 20 defines an internal elongate cavity 22 that extends substantially along the length of the body from a proximal end 26 towards distal end 24. The distal end 24 of the syringe body 20 comprises a nozzle or tip 28 with a discharge lumen in fluid communication with the internal elongate cavity 22. The tip 28 of the syringe body 20 is preferably adapted for connection to the distal end 71 of the gastric relief tube 69 (as depicted in FIG. 1). The proximal end 26 of the syringe body 20 includes an opening 30 for receiving the plunger 40 therein. In an example embodiment, the syringe is a 100 mL syringe. The syringe body 20 can have a substantially circular cross-section or can comprise a non-circular, oval, elliptical, rectangular, or asymmetric cross-section as desired.

The plunger 40 includes an elongated body 41 sized to be inserted into the opening 30 of the syringe body 20, the body or arm having a distal end 42 and a proximal end 44. The distal end 42 comprises a sealing head 45 for tightly engaging an inner wall of the body cavity 22. The sealing head and/or gasket 45 substantially mirrors the cross-section and diameter of the cavity 22 to provide an appropriate seal between the head and the cavity. In example embodiments, the sealing head 45 frictionally engages the inner wall of the cavity 22, such that the plunger 40 remains in a particular position within the syringe body 20 absent user manipulation. The plunger body 41 also comprises at least one, and preferably two or more ribs 47 that extend to fit within the cross-section and/or diameter of the cavity 22. Thus, as the plunger 40 is selectively inserted into the cavity 22 of the syringe body 20 and travels therein during use, the ribs 47 operate to keep the plunger 40 aligned within the cavity 22 and prevent the plunger from tipping within the same. As such, the ribs 47 help maintain an adequate seal between the plunger head 45 and the wall of the cavity 22. The proximal end 44 the plunger 40 includes a contact face 48 to permit user manipulation.

In order to permit the enteral reflux collection syringe 80 of the present invention to be vented during use (without fully removing the plunger 40 from the syringe body 20), the syringe body includes one or more vents 50. The vents 50 permit the passage of air into the syringe body cavity 22 when in use. In the depicted example embodiments, each vent 50 comprises a channel 52 that extends from the proximal end 26 of the syringe barrel along a portion of the barrel's length, into the inner cavity 22 of the syringe body 20. While example depicted embodiments depict four vents 50, alternative embodiments can include one vent, two vents, three vents, or five or more vents as desired. The syringe plunger is selectively positionable within the barrel in one or more closed/unvented positions (FIGS. 2, 3A and 4) where the contained volume within the syringe is sealed to prevent air passage in or out, or one or more open/vented positions (FIG. 3B) wherein air can pass in and out of the syringe.

In example embodiments, the enteral reflux collection system 60 comprises one or more food-grade plastics (i.e. polypropylene), other polymers, glass, metals, metal alloys, resins, rubbers, rubber derivatives, elastomerics (i.e. santoprene), silicones or other materials of construction. Optionally, colorants and/or other additives may be included. The syringe can include external markings or other indicia, for example to indicate volume capacity and/or content levels.

In operation, the collection system 60 of the present invention can be used to deliver fluids to a subject, and to selectively collect, prevent collection, and/or induce aspiration of the gastric reflux fluids during enteral feeding. For preventing the collection of gastric reflux fluids, as shown in FIG. 3A, the plunger 40 can be positioned within the syringe body 20 in a closed position. Alternately, for inducing aspiration of gastric fluids, the plunger 40 can be moved further into the syringe body 20 where as the plunger head 45 is advanced or retracted, increased pressure or suction alternatively develops to alleviate a clog within the reflux tube. Additionally, the collection of gastric fluids is enabled by positioning the syringe in its vented state as shown in FIG. 3B. As a result, the enteral reflux collection system 80 of the present invention is multi-functional, selectively providing ventilation, vacuum, and/or suction.

While the invention has been described with reference to preferred and example embodiments, it will be understood by those skilled in the art that a variety of modifications, additions and deletions are within the scope of the invention, as defined by the following claims.

What is claimed is:

1. An enteral reflux collection system comprising:
a fluid container comprising a discharge;
an enteral feeding tube for delivering fluid from the fluid container;
a vented reflux collection syringe comprising a syringe barrel defining an internal cavity and a syringe plunger movable within the syringe barrel between a first position and a second position, the syringe barrel comprising at least one elongate vent channel formed therein, and the syringe plunger comprising a sealing head configured to seal and prevent air passage in or out of the internal cavity when the syringe plunger is in the first position and to allow venting of air in or out of the internal cavity through the at least one vent channel when the syringe plunger is in the second position; and
a reflux relief tube coupled to the enteral feeding tube for delivering reflux to the vented reflux syringe.

2. The enteral reflux collection system of claim 1, wherein the vented reflux collection syringe is configured to be positioned at a higher elevation than the fluid container discharge.

3. The enteral reflux collection system of claim 1, further comprising a coupling to couple the reflux relief tube and the enteral feeding tube.

4. The enteral reflux collection system of claim 3, wherein the coupling comprises a Y-connector.

5. The enteral reflux collection system of claim 1, wherein the vented collection syringe comprises four elongate vent channels.

6. The enteral reflux collection system of claim 1, wherein the vented collection syringe is configured to have a reflux collection state and a reflux prevention state.

7. An enteral reflux collection system comprising:
a fluid container comprising a discharge;
an enteral feeding tube for delivering a fluid from the fluid container;
a vented reflux collection syringe comprising a syringe body defining an internal chamber and a plunger translatably mounted therein, the syringe body comprising at least one elongate vent channel formed therein, the plunger configured to form a seal with the syringe body and prevent venting to and from the internal chamber through the at least one elongate vent channel when the plunger is in a first position, and configured to allow venting to and from the internal chamber through the at least one elongate vent channel when the plunger is in a second position; and
a reflux relief tube between the enteral feeding tube and the vented reflux syringe.

8. The enteral reflux collection system of claim 7, wherein the internal chamber is generally cylindrical in shape.

9. The enteral reflux collection system of claim 7, wherein the at least one elongate vent channel comprises a plurality of vent channels extending from a proximal end of the syringe body toward a distal end thereof.

10. The enteral reflux collection system of claim 7, wherein the vented reflux collection syringe is configured to be positioned at a higher elevation than the fluid container discharge.

11. The enteral reflux collection system of claim 7, further comprising a coupling to couple the reflux relief tube and the enteral feeding tube.

12. The enteral reflux collection system of claim 11, wherein the coupling comprises a Y-connector.

13. The enteral reflux collection system of claim 7, wherein the vented collection syringe comprises four elongate vent channels.

14. The enteral reflux collection system of claim 7, wherein the vented collection syringe is configured to have a reflux collection state and a reflux prevention state.

15. An enteral reflux collection system comprising:
a fluid container comprising a discharge;
an enteral feeding tube for delivering fluid from the fluid container;
a vented reflux collection syringe comprising a syringe body defining an internal cavity and a plunger movable within the syringe body between a reflux collection state and a reflux prevention state, the syringe body comprising at least one elongate vent channel allowing venting to and from the internal cavity through the at least one elongate vent channel when the plunger is in the reflux collection state, and preventing venting to and from the internal cavity when the plunger is in the reflux prevention state.

* * * * *